US011235151B2

(12) United States Patent
Greenberg et al.

(10) Patent No.: US 11,235,151 B2
(45) Date of Patent: Feb. 1, 2022

(54) PATTERN DETECTION AND LOCATION IN A PROCESSED IMAGE

(71) Applicant: Second Sight Medical Products, Inc., Sylmar, CA (US)

(72) Inventors: Robert J Greenberg, Los Angeles, CA (US); Avraham I Caspi, Rehovot (IL); Francesco Merlini, Lausanne (CH); Arup Roy, Los Angeles, CA (US)

(73) Assignee: Second Sight Medical Products, Inc, Sylmar, CA (US)

( * ) Notice: Subject to any disclaimer, the term of this patent is extended or adjusted under 35 U.S.C. 154(b) by 177 days.

(21) Appl. No.: 16/519,855

(22) Filed: Jul. 23, 2019

(65) Prior Publication Data

US 2019/0347475 A1 Nov. 14, 2019

Related U.S. Application Data

(62) Division of application No. 15/801,861, filed on Nov. 2, 2017, now Pat. No. 10,410,047, which is a division
(Continued)

(51) Int. Cl.
| | |
|---|---|
| *A61N 1/36* | (2006.01) |
| *A61B 5/1171* | (2016.01) |
| *A61F 9/08* | (2006.01) |
| *G06K 9/00* | (2006.01) |
| *G06K 9/46* | (2006.01) |

(52) U.S. Cl.
CPC ........ *A61N 1/36046* (2013.01); *A61B 5/1176* (2013.01); *A61F 9/08* (2013.01); *A61N 1/36185* (2013.01); *G06K 9/00228* (2013.01); *G06K 9/00288* (2013.01); *G06K 9/4671* (2013.01)

(58) Field of Classification Search
None
See application file for complete search history.

(56) References Cited

U.S. PATENT DOCUMENTS

| 4,573,481 A | 3/1986 | Bullara |
| 4,628,933 A | 12/1986 | Michelson |

(Continued)

FOREIGN PATENT DOCUMENTS

WO    WO 200103/84465    4/2011

OTHER PUBLICATIONS

Herpers, R. et al. "Detection and tracking of faces in real environments." International Workshop on Recognition, et al, 1999, IEEE Proceedings.
(Continued)

*Primary Examiner* — Kennedy Schaetzle
(74) *Attorney, Agent, or Firm* — Scott Dunbar

(57) ABSTRACT

The present invention is a method of processing a video image in an electronic video processor, including the steps of receiving an input image having an input field of view, generating a processed image from the input image, and having an output field of view smaller than the input field of view, searching for a predetermined pattern within the input image, providing an indication when the predetermined pattern is found in the input image, zooming the processed image to the input field of view and highlighting the predetermined pattern in the processed image in response to the indication.

12 Claims, 16 Drawing Sheets

Related U.S. Application Data of application No. 15/357,880, filed on Nov. 21, 2016, now Pat. No. 9,842,248, which is a division of application No. 14/825,043, filed on Aug. 12, 2015, now Pat. No. 9,526,896.

(60) Provisional application No. 62/036,463, filed on Aug. 12, 2014.

(56) References Cited

U.S. PATENT DOCUMENTS

| | | | |
|---|---|---|---|
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,108,437 A | 8/2000 | Lin | |
| 6,400,989 B1 | 6/2002 | Eckmiller | |
| 6,458,157 B1 | 10/2002 | Suanlng | |
| 7,038,577 B2 | 5/2006 | Pawlicki et al. | |
| 7,937,667 B2 | 5/2011 | Kramer et al. | |
| 8,271,091 B2 | 9/2012 | McMahon et al. | |
| 8,274,572 B2 | 9/2012 | Okamoto et al. | |
| 9,571,675 B2 | 2/2017 | Wang | |
| 9,715,751 B2 | 6/2017 | Bhatt | |
| 2005/0063566 A1* | 3/2005 | Beek | A61B 5/1176 382/115 |
| 2006/0215924 A1* | 9/2006 | Steinberg | H04N 5/232945 382/254 |
| 2008/0058894 A1 | 3/2008 | Dewhurst | |
| 2008/0183244 A1 | 7/2008 | Greenberg | |
| 2010/0249878 A1 | 9/2010 | McMahon et al. | |
| 2012/0212594 A1* | 8/2012 | Barnes | G06K 9/605 348/62 |
| 2013/0035742 A1 | 2/2013 | Talbot et al. | |
| 2013/0083153 A1 | 4/2013 | Lindbergh et al. | |
| 2013/0310933 A1* | 11/2013 | Cho | A61N 1/36046 623/6.63 |
| 2014/0240511 A1 | 8/2014 | Nystrom et al. | |
| 2015/0002808 A1* | 1/2015 | Rizzo, III | G02C 11/10 351/158 |
| 2016/0325096 A1* | 11/2016 | Lui | G06K 9/4604 |

OTHER PUBLICATIONS

Assoc. for Research in Vision and Opthalmology, ARVO 2011 Abstract Search and Itinerary Builder: Face Detection, et al. May 4, 2011.

* cited by examiner

PATTERN DETECTION AND LOCATION IN A PROCESSED IMAGE

CROSS REFERENCE TO RELATED APPLICATIONS

This application is a divisional application of U.S. patent application Ser. No. 15/801,861, filed Nov. 2, 2017 for Pattern Detection and Location in a Processed Image, which is a divisional application of U.S. patent application Ser. No. 15/357,880, filed Nov. 21, 2016, for Pattern Detection and Location in a Processed Image, now U.S. Pat. No. 9,842,248, which is a divisional application of U.S. patent application Ser. No. 14/825,043, filed Aug. 12, 2015, for Pattern Detection and Location Indication for a Visual Prosthesis, now U.S. Pat. No. 9,526,896, which claims priority to, benefit of, and incorporates by reference, U.S. Provisional Application 62/036,463, filed Aug. 12, 2014 for Visual Prosthesis.

FIELD OF THE INVENTION

The present invention is generally directed to an improved method of processing an image.

BACKGROUND OF THE INVENTION

Detection and Tacking of Faces in Real Environments by R. Herpers, et. al. from International Workshop on Recognition, Analysis and Tracking of Faces and Gestures in Real-Time Systems, 1999, IEEE Proceedings describes basics of facial detection and recognition software for general applications.

Xuming He presented an ARVO poster in 2011 describing a system for a visual prosthesis that automatically zooms in on a face in a visual scene to help a visual prosthesis user identify the face.

US Patent Application 20080058894 for Audio-tactile Vision Substitution System to Dewhurst describes providing visual information to a vision impaired person using audio or tactile information including information regarding facial characteristics.

International patent application WO 20010384465 for Object Tracking for Artificial Vision by Barns, et al. describes a system for tracking objects, such as a face, for a visually impaired user.

US Patent application 20130035742 for Face Detection Tracking and Recognition for a Visual Prosthesis, the disclosure of which is incorporated herein by reference, is by the present applicants and describes a system for identifying a face and indicating its location to the user of a visual prosthesis.

SUMMARY OF THE INVENTION

The present invention is a method of processing a video image in an electronic video processor, including the steps of receiving an input image having an input field of view, generating a processed image from the input image, and having an output field of view smaller than the input field of view, searching for a predetermined pattern within the input image, providing an indication when the predetermined pattern is found in the input image, zooming the processed image to the input field of view and highlighting the predetermined pattern in the processed image in response to the indication.

BRIEF DESCRIPTION OF THE DRAWINGS

FIGS. 11-1, 11-2, 11-3 and 11-4 show an exemplary embodiment of a video processing unit. FIG. 11-1 should be viewed at the left of FIG. 11-2. FIG. 11-3 should be viewed at the left of FIG. 11-4. FIGS. 11-1 and 11-2 should be viewed on top of FIGS. 11-3 and 11-4.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

An aspect of the invention is a method of aiding a visual prosthesis user, including detecting a face in the user's visual scene and communicating the location of the detected face, including zooming out to show the location of the detected face through a highlight; and providing cues to the user regarding a detected face. The cue may include sound, vibration, stating a name associated with the detected face, highlighting the detected face, zooming in on the detected face, or tactile feedback. The method may further include looking up the detected face in a look up table to provide a name associated with the detected face. The cue may further include an indication of if the face is looking toward the user, to the side or looking away. A further aspect of the invention is including information about a facial characteristic in the cue. Facial characteristics may include gender, size, distance, head movement, or other body motion. All of these characteristics are controllable by the user through controls on the video processing unit worn on the body.

Figure 1A:
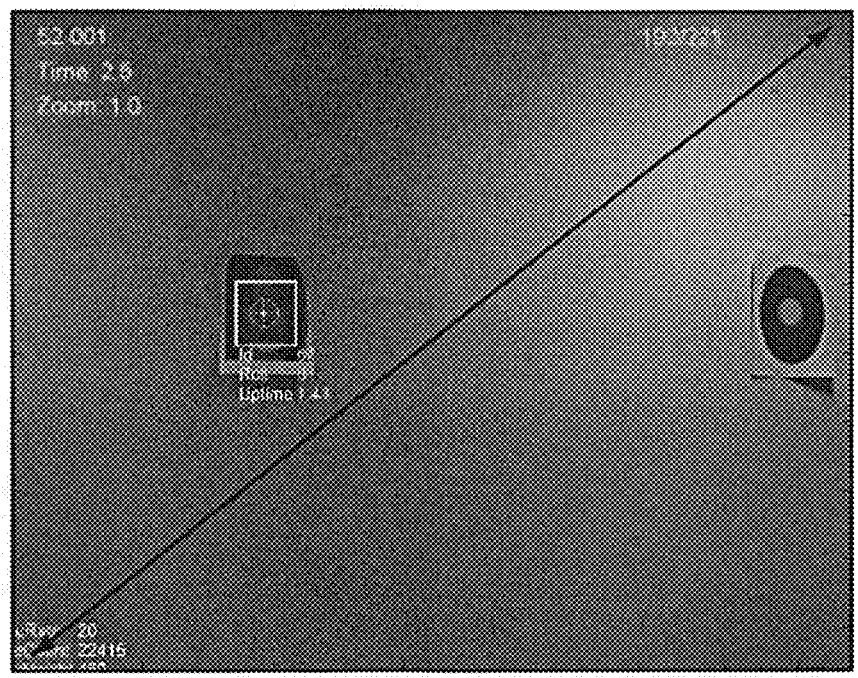
FIG. 1A is an experimental face detection setup as seen through the camera of a visual prosthesis with a 53 degree field of view.
Figure 1B:
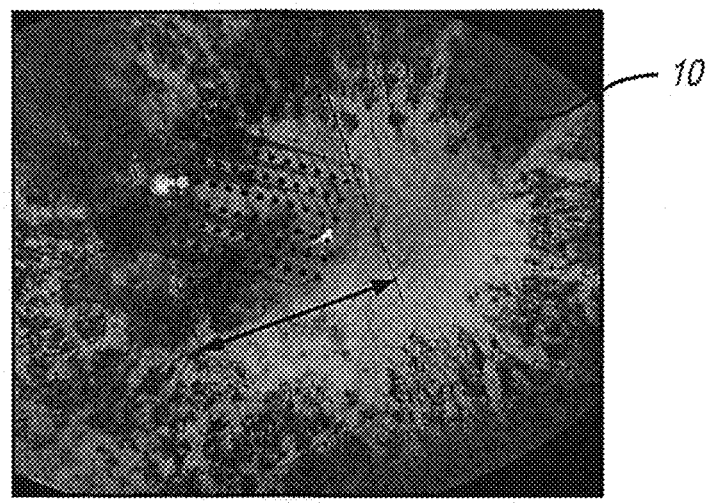
FIG. 1B is a photograph of an electrode array on a retina showing the 20 degree field of view covered by the electrode array.
Figures 1, 11:
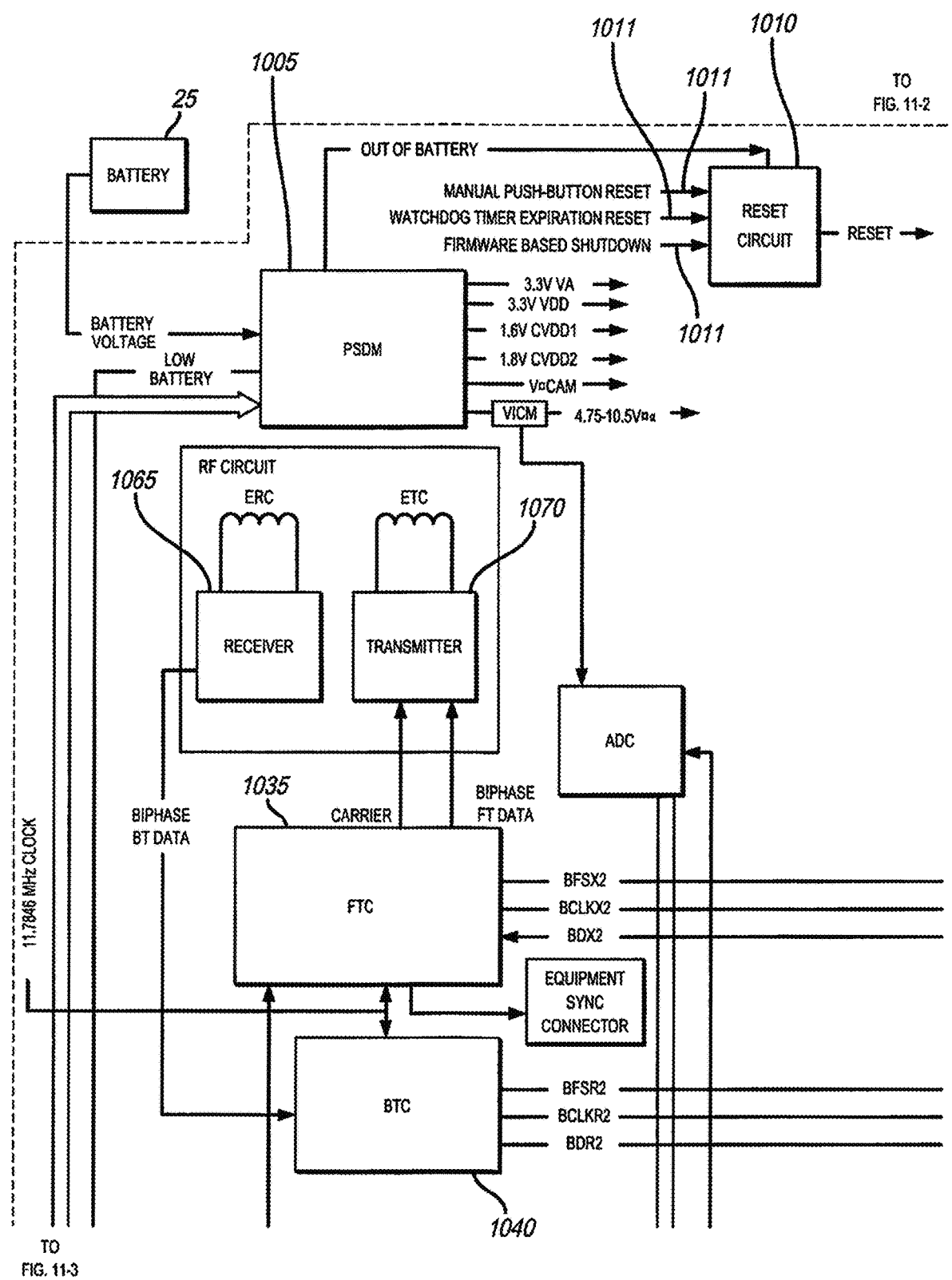

Referring to FIG. 1, The currently available visual prosthesis provides an electrode array 10 which stimulates the retina to provide a field of view of 20 degrees (FIG. 1A) while a camera provides a 53 degree field of view (FIG. 1B). While larger arrays are desirable and will be available in the future, it is clear that camera technology will always surpass electrode array technology. Zoom systems have been provided in visual prostheses. A one to one ratio is best for locomotion and hand eye coordination as described in US-2008-0183244-A1, Field of View Matching in a Visual Prosthesis. It is also known that zoom in can be beneficial for tasks such as reading. However, the facial detection task benefits from a wider angle view. It is often beneficial for a visual prosthesis user to know the location of faces within a scene. Those faces can be identified with a simple highlight or only stimulating the location of the face. In such case a wider field of view supports finding faces quickly. It should be clear that while described in relation to facial detection, any pattern of interest can be detected and its location identified by the same method. Patterns of interest may include, for example, stumble or trip hazards, automobiles, doors, windows or faces.

It is not necessary to zoom the user's view to detect and identify such patterns. In this example, the camera views 53 degrees while only 20 degrees is presented to the user through an electrode array. Software can be constantly scanning the 53 degree image and notifying the user when a pattern of interest is detected in the scene. When a pattern of interest is detected, the system can zoom out and cue a user, or cue a user and wait for the user to zoom out manually. It is important to not change the field of view without the user's knowledge.

This function can be further combined with recognition functions such as looking up a detected face and speaking the name associated with the face. Alternatively, the system can describe characteristics of the face.

Figures 2, 11:
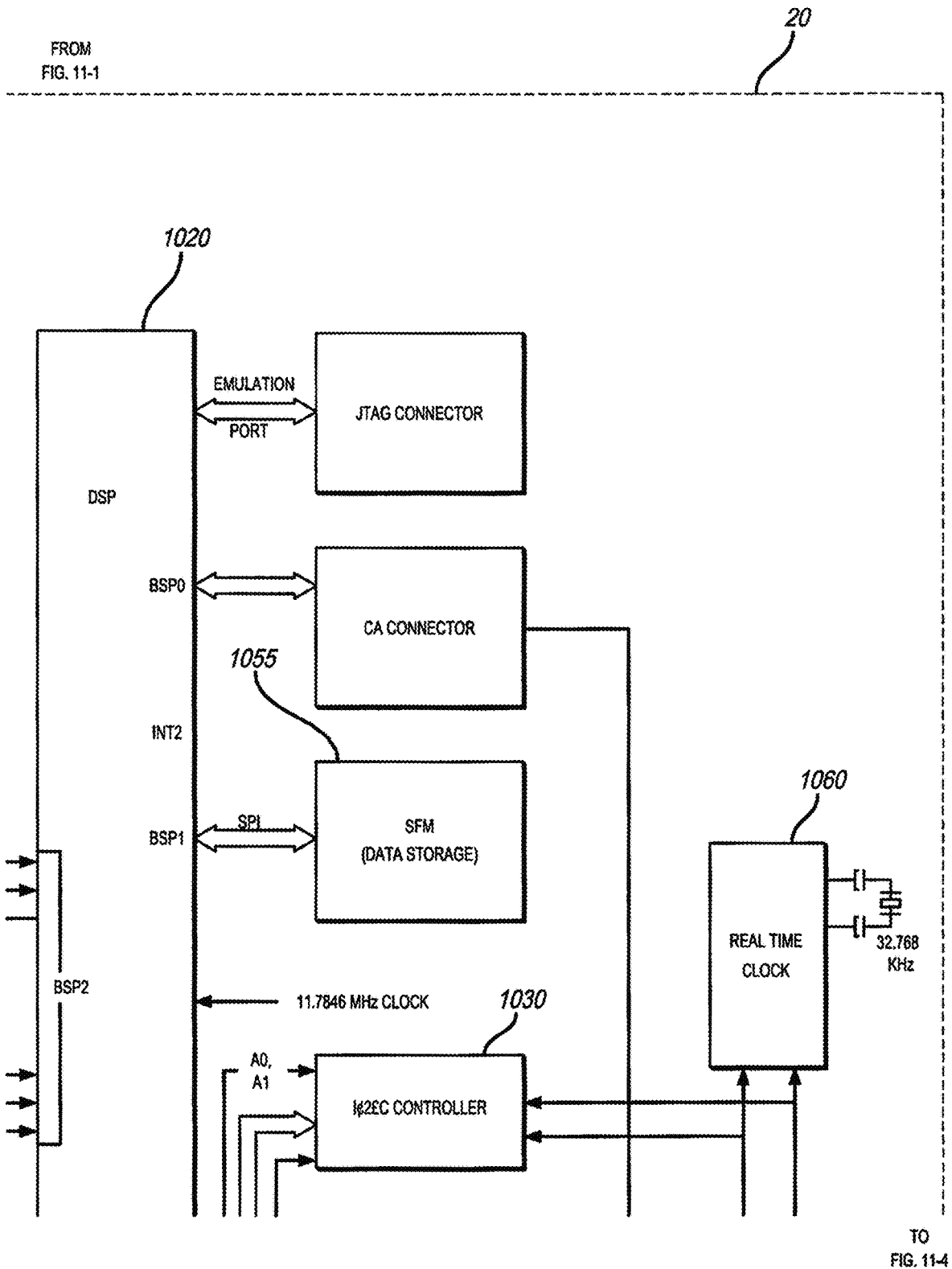
Figures 3, 11:
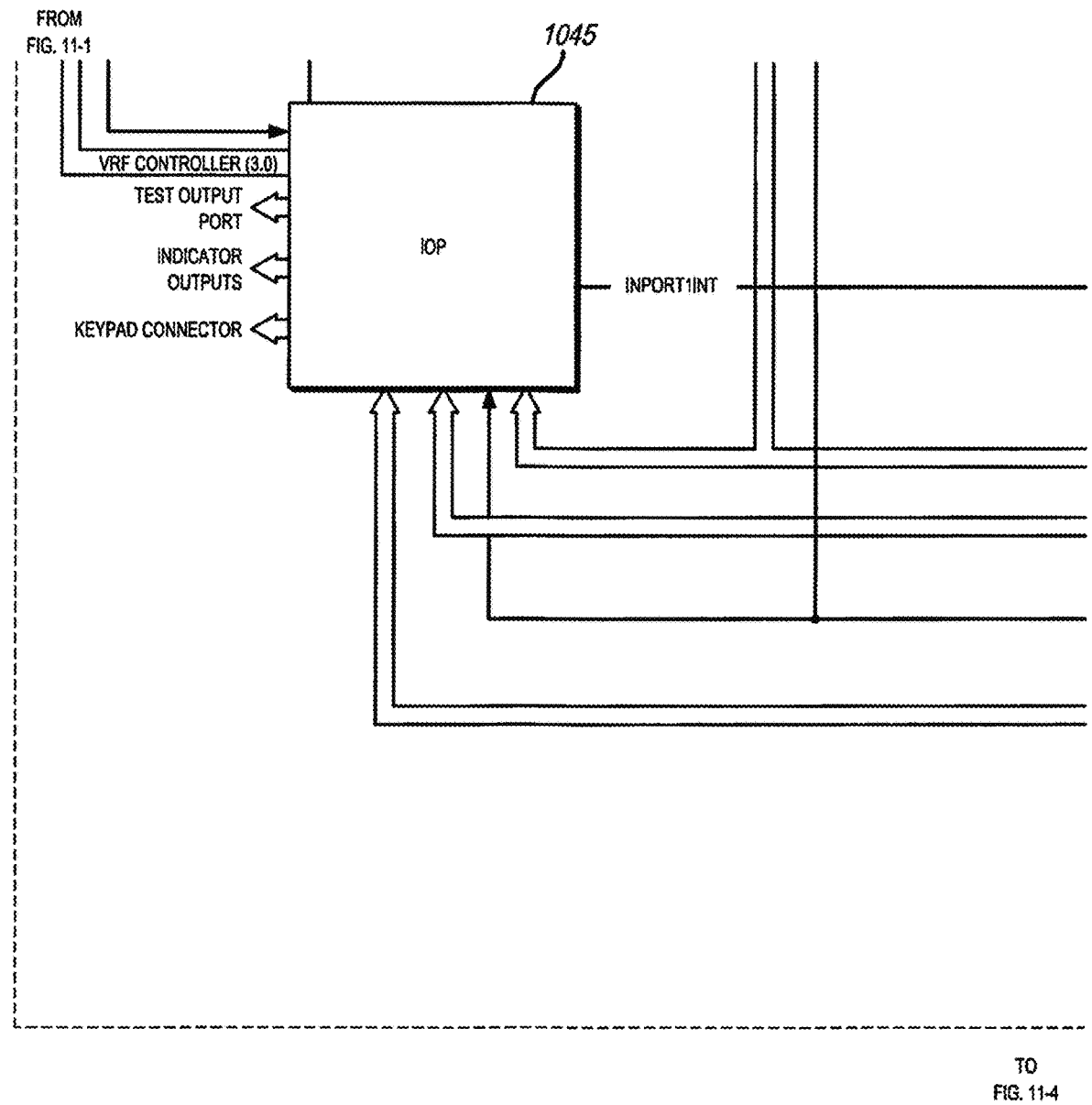
Figures 4, 11:
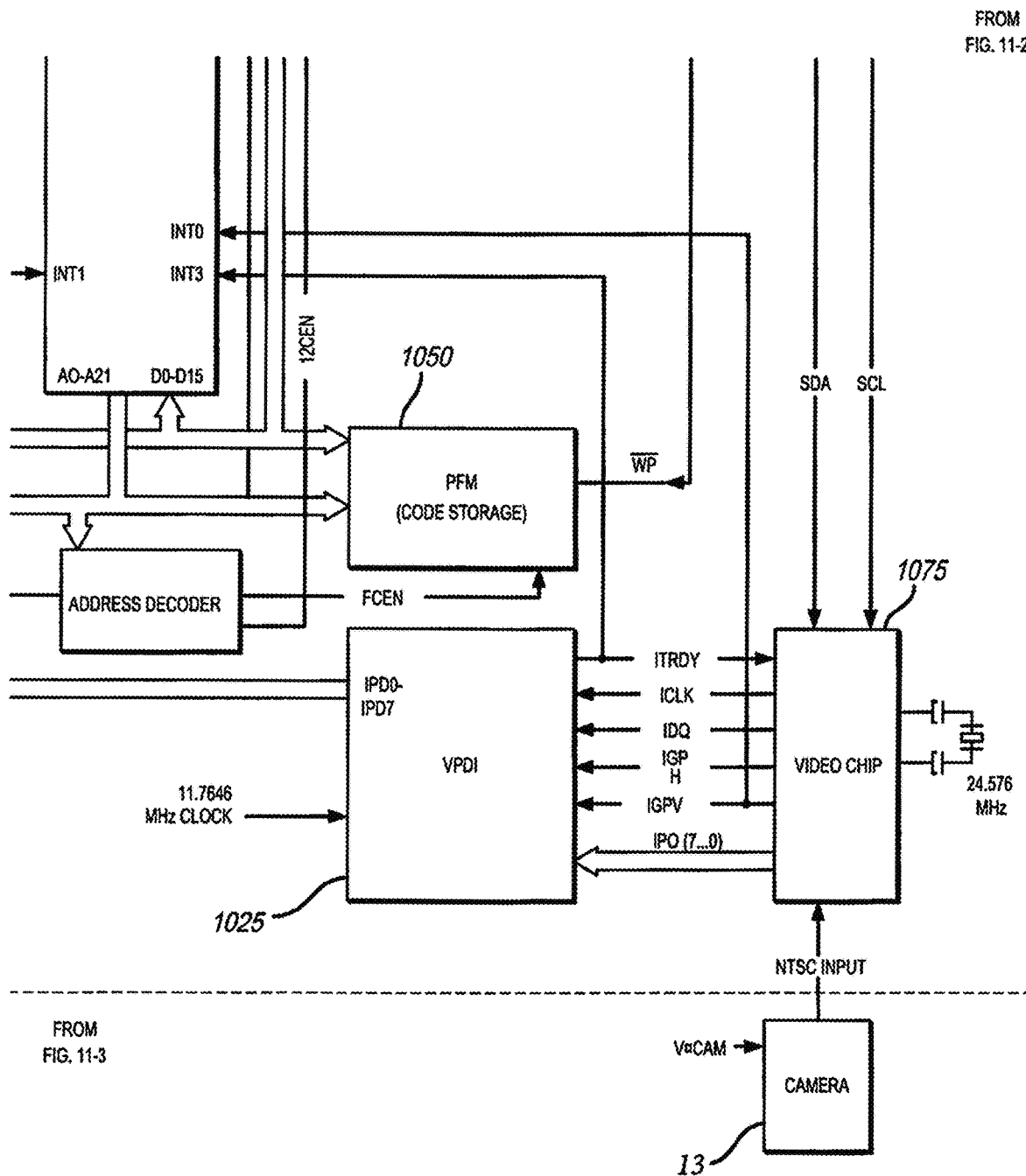

Referring to FIG. 2, the experimental face detection setup is shown as seen through the camera of a visual prosthesis, showing the narrower field of view 2000 to the electrode array 10. A face is detected 2002 and electrodes stimulated by a face detection filter 2004. The additional information provided by the face detection filter is minimal. A visual prosthesis user will need to scan the scene through the 20 degree view until a face is detected. At this level the visual prosthesis user would probably be able to detect a face without the filter.

Figure 2A:
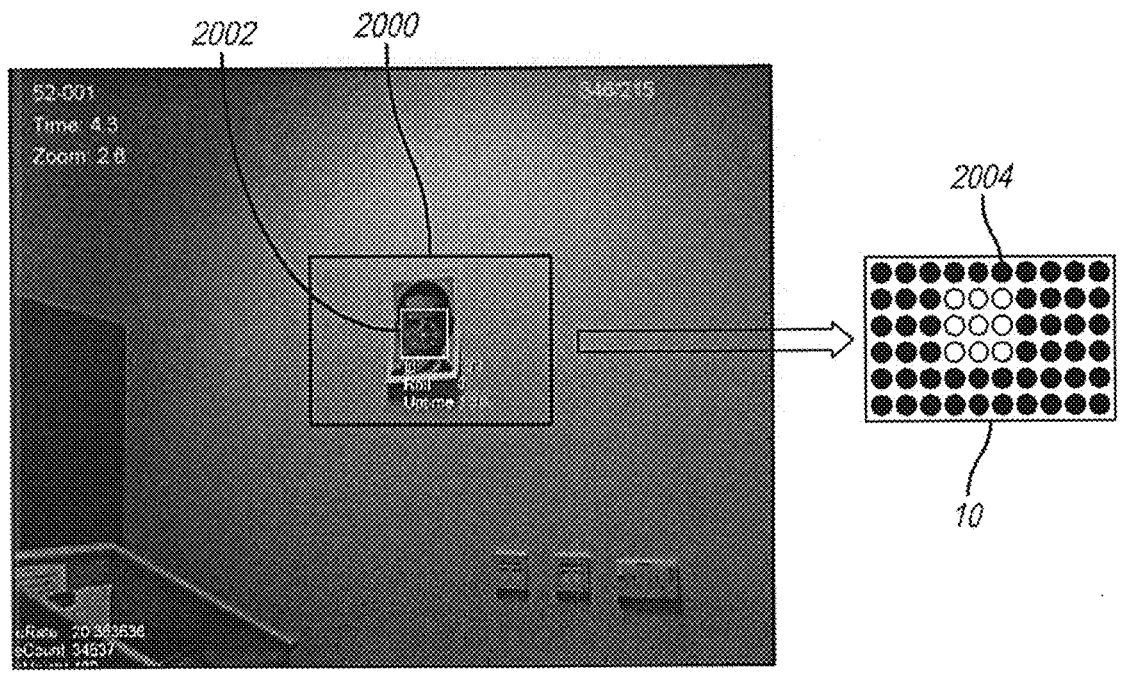
FIG. 2A is an experimental face detection setup as seen through the camera of a visual prosthesis, showing the narrower field of view to the electrode array, and the electrodes stimulated by a face detection filter.
Figure 2B:
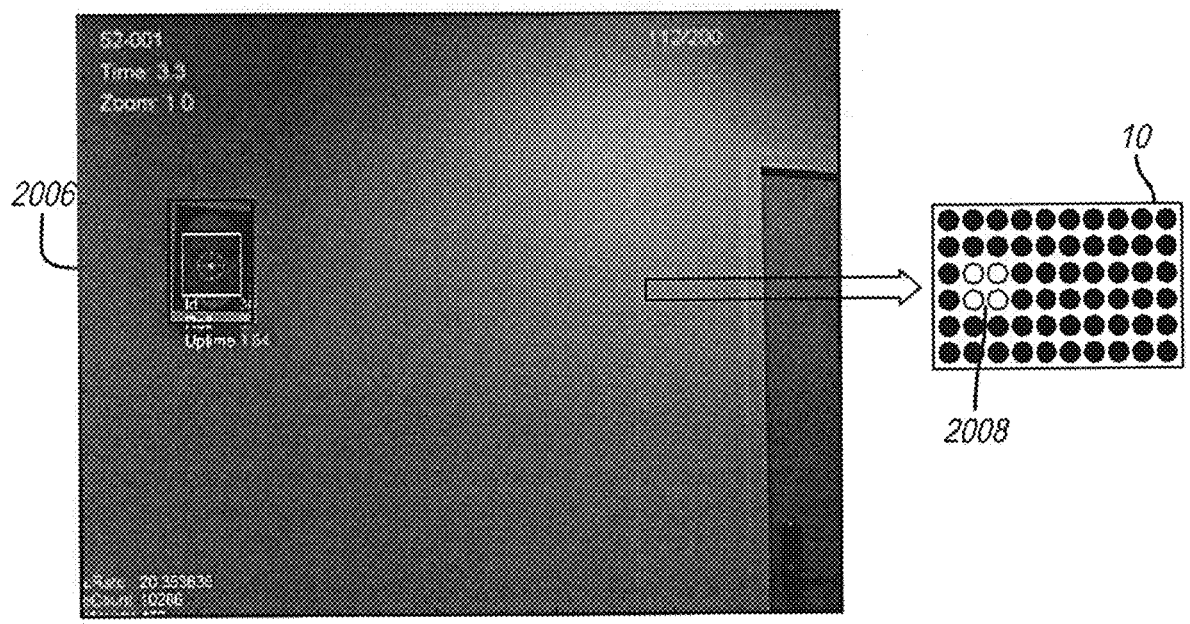
FIG. 2B is an experimental face detection setup as seen through the camera of a visual prosthesis, showing the wider field of view of the camera mapped to the electrode array, and the electrodes stimulated by a face detection filter.

Referring to FIG. 2B, the experimental face detection setup is shown as seen through the camera of a visual prosthesis. In this case, the wider field of view of the camera is mapped to the electrode array 10. A face is detected 2006 by a face detection filter and electrodes are stimulated 2008. With the wider field of view, the visual prosthesis user is able to identify the location of a face within the scene with minimal or no scanning. Preferably, a visual prosthesis user would be able to switch modes quickly and easily. For example, a single button could be provided on the VPU which shifts to the wider field of view and activating the face detection software. Releasing the button would return the visual prosthesis to the previous mode. This allows the user, when entering a room for example, to quickly identify the location of faces in the room.

While described in terms of face detection, the present invention, in particular as it applies to wide field of view, is also applicable to wide range of other uses, such as hazard detection. Any item that can be detected by the visual prosthesis camera and image processing software can be readily identified with the present invention. As another example, when combined with an infrared camera, heat sources can be identified.

The following table shows face detection response times in a clinical trial.

| User ID | Wide FOV (53 deg.) | Normal FOV (20 deg.) |
|---------|--------------------|-----------------------|
| 1       | 38 ± 4             | 53 ± 12               |
| 2       | 20 ± 2             | 42 ± 5                |
| 3       | 5 ± 1              | 11 ± 3                |
| 4       | 12 ± 2             | 22 ± 4                |

The times are in seconds based on 10 trials for each user after 10 practice trials. Another trial was conducted with and without a target (target turned away not showing their face.

| User ID | Mean Response Time |
|---------|--------------------|
| 1       | 5.2 ± .9           |
| 2       | 6.4 ± .7           |

Figure 3:
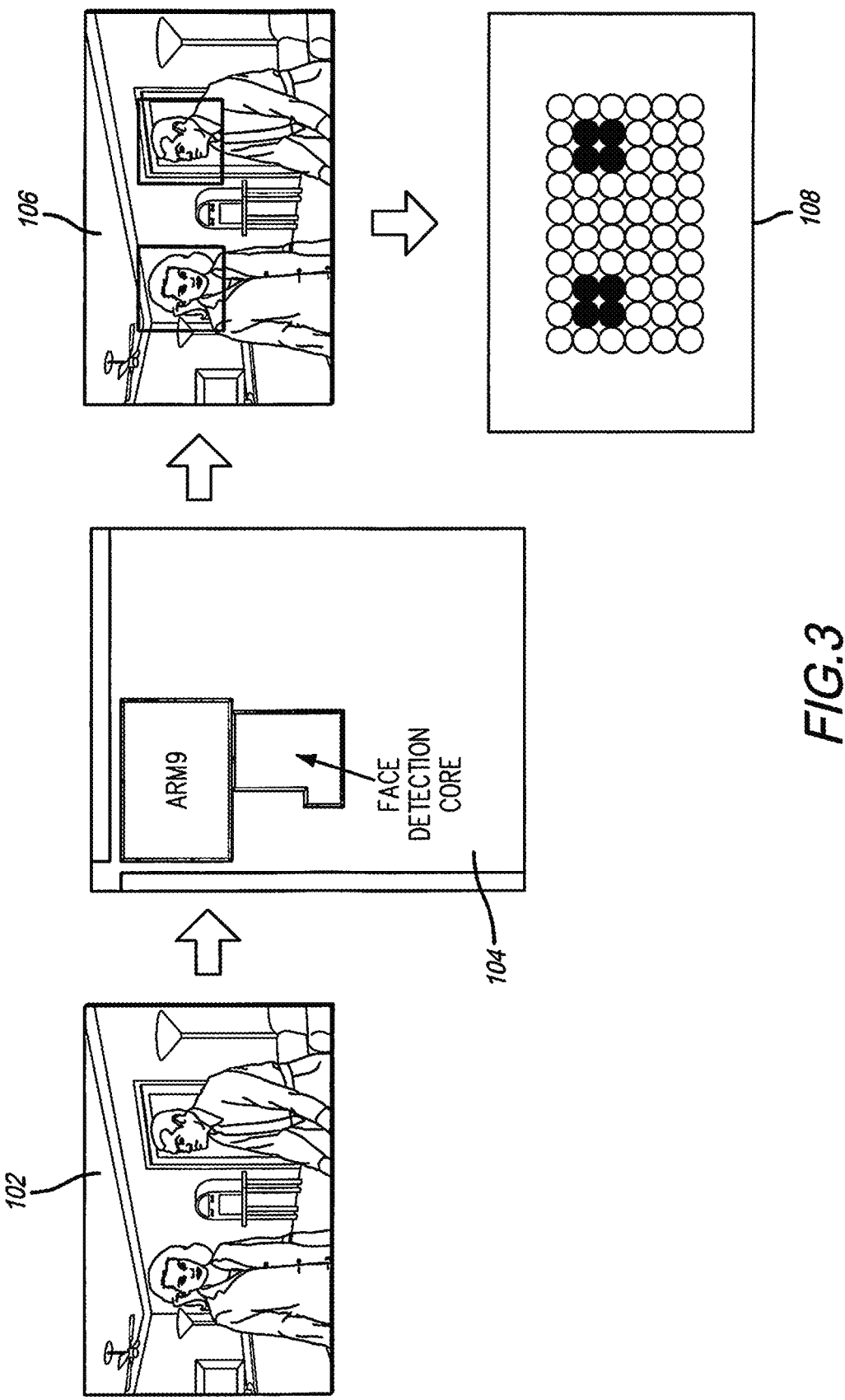
FIG. 3 is a flowchart showing facial detection.

Referring to FIG. 3, simple face tracking can be a significant benefit to a blind person. The presence of multiple faces may be also relayed. The process flow of basic face detection and tracking is provided. The video processor records a visual scene 102, show here with two faces. The video processor draws a square around a detected face 104. The video processor draws squares around both face units and draws a smaller square around the identifiable portions of the two faces for recognition processing 106. Even with a very low resolution electrode array, it is possible for a user to locate the faces 108 to improve interaction with the other people.

Figure 4:
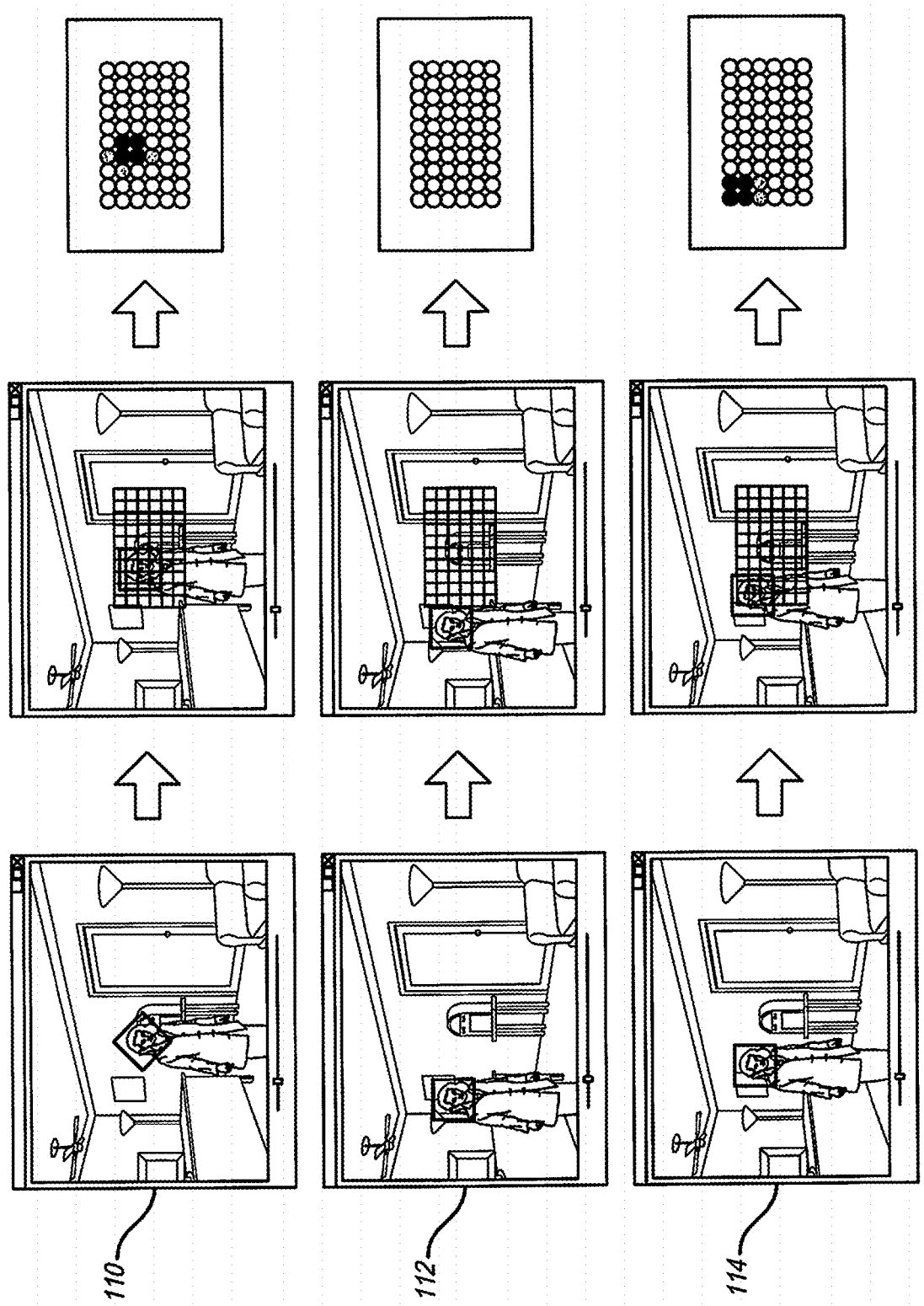
FIG. 4 is a set of three flowcharts equating face detection response to square localization.

Referring to FIG. 4, square localization is a common task preformed by visual prosthesis users. See US Patent Application 2010/0249878, for Visual Prosthesis Fitting Training and Assessment System and Method, filed Mar. 26, 2010 which is incorporated herein by reference. Providing a square over a detected face, simplifies the face tracking to the level of square localization. In the first example 110, the face is identified at an angle. It may be advantageous to straighten the square to improve user recognition. In the second example 112, the face is outside the visual scene so no highlight is provided. In the third example 114, the face square is simply highlighted without modification. The distance to the person, distance direction and velocity may also be relayed to the user.

Figure 5:
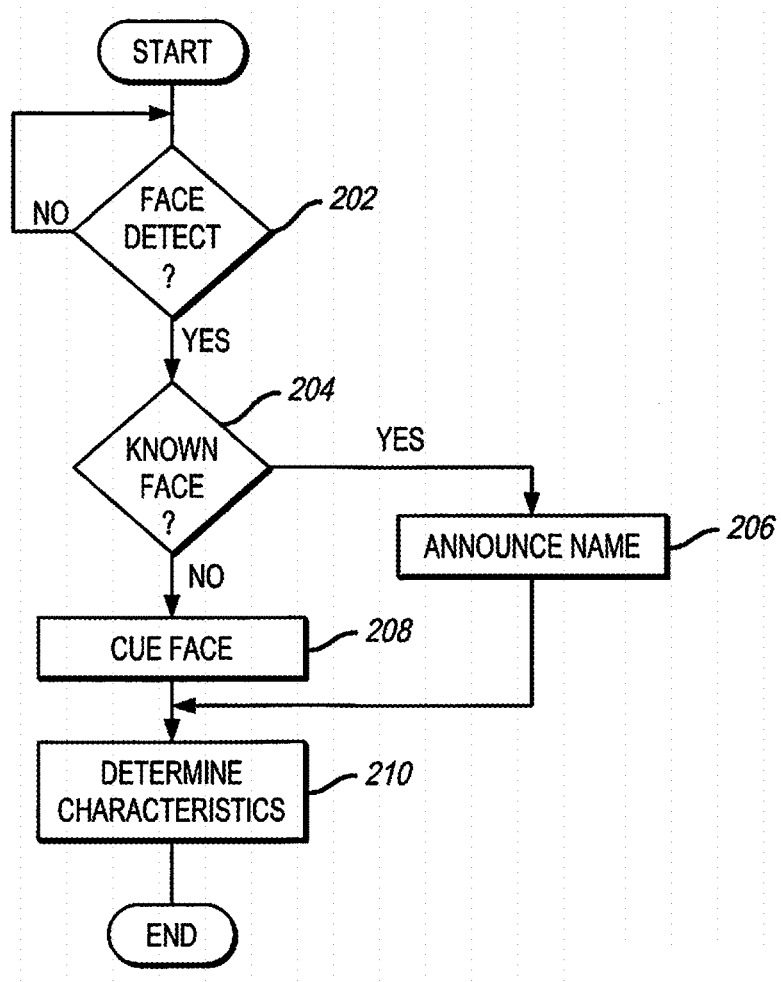
FIG. 5 is a flowchart showing the process of face detection and recognition.

Referring to FIG. 5, the process of face detection begins by scanning the input image from the camera for a pattern of a face 202. There are many well known processes for identifying faces in an image. If a face is detected, it is compared to a database of known faces 204. If the face is unknown, the face is cued 208 as described in greater detail in FIG. 6. If the face is known, it is announced 206. Finally, facial characteristics are determined 210.

Figure 6:
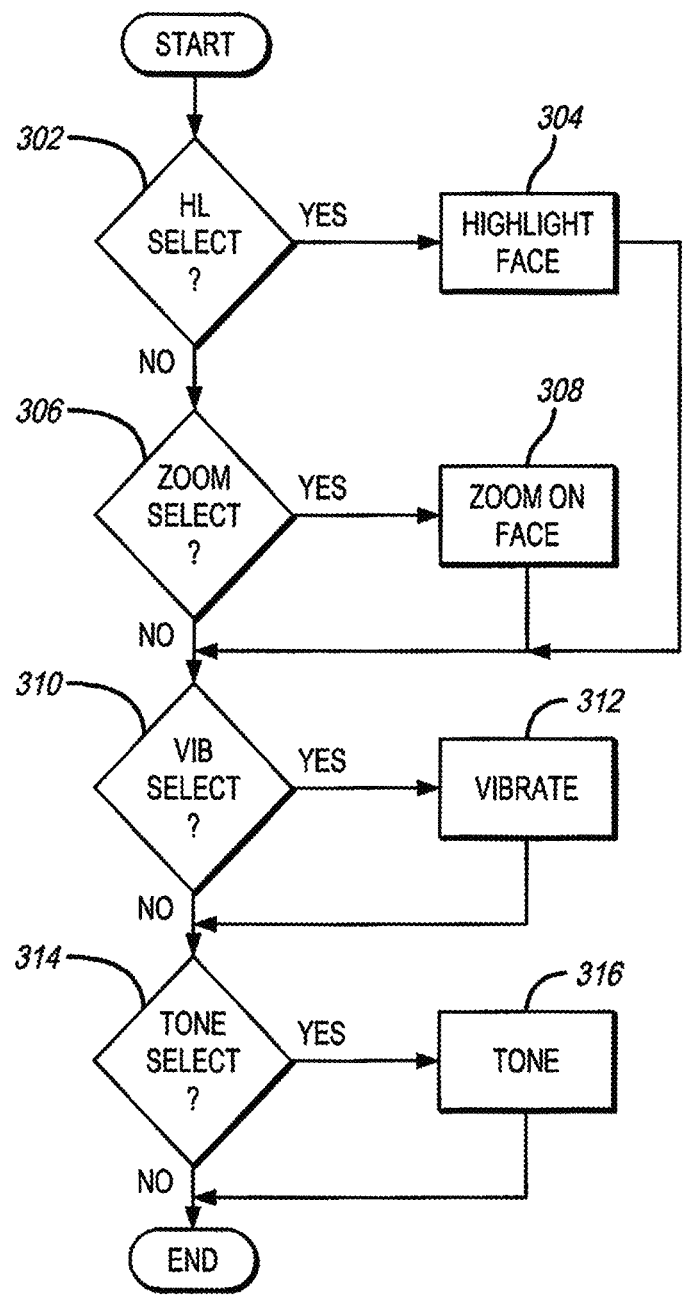
FIG. 6 is a flowchart showing the process of face cueing.

Referring to FIG. 6, there are several options for cueing the presence of an unknown face which are selectable by the user. The user can change the selection by activating controls on the VPU 20. The system determines if Highlight is selected 302, and highlights the face 304. In a low resolution visual prosthesis this can be accomplished simply by replacing the face with a bright image. In a higher resolution visual prosthesis this may be accomplished by marking a square or circle around the face. Alternatively, if Zoom is selected 306, the visual prosthesis zooms in on the face aiding the user in identifying the face 308, or zooming out to provide the location of the face. If Vibration is selected 310, the visual processing unit vibrates (like a cell phone in silent mode) 312. If Tone is selected 314, the speaker on the visual prosthesis emits a tone 316. Note that the cues may be used in combination such as highlight, vibrate and tone.

Figure 7:
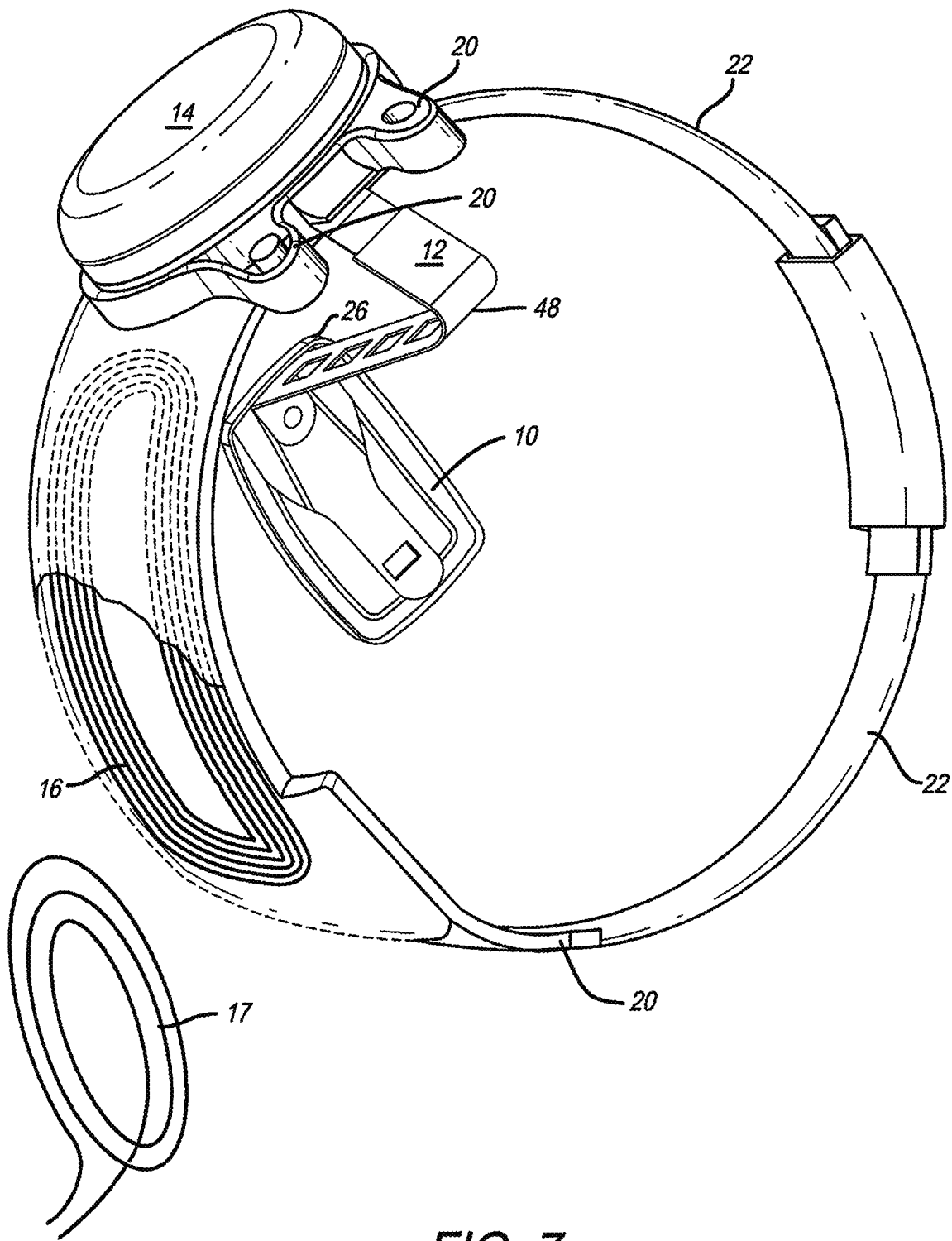
FIG. 7 is a perspective view of the implanted portion of the preferred visual prosthesis.
Figure 8:
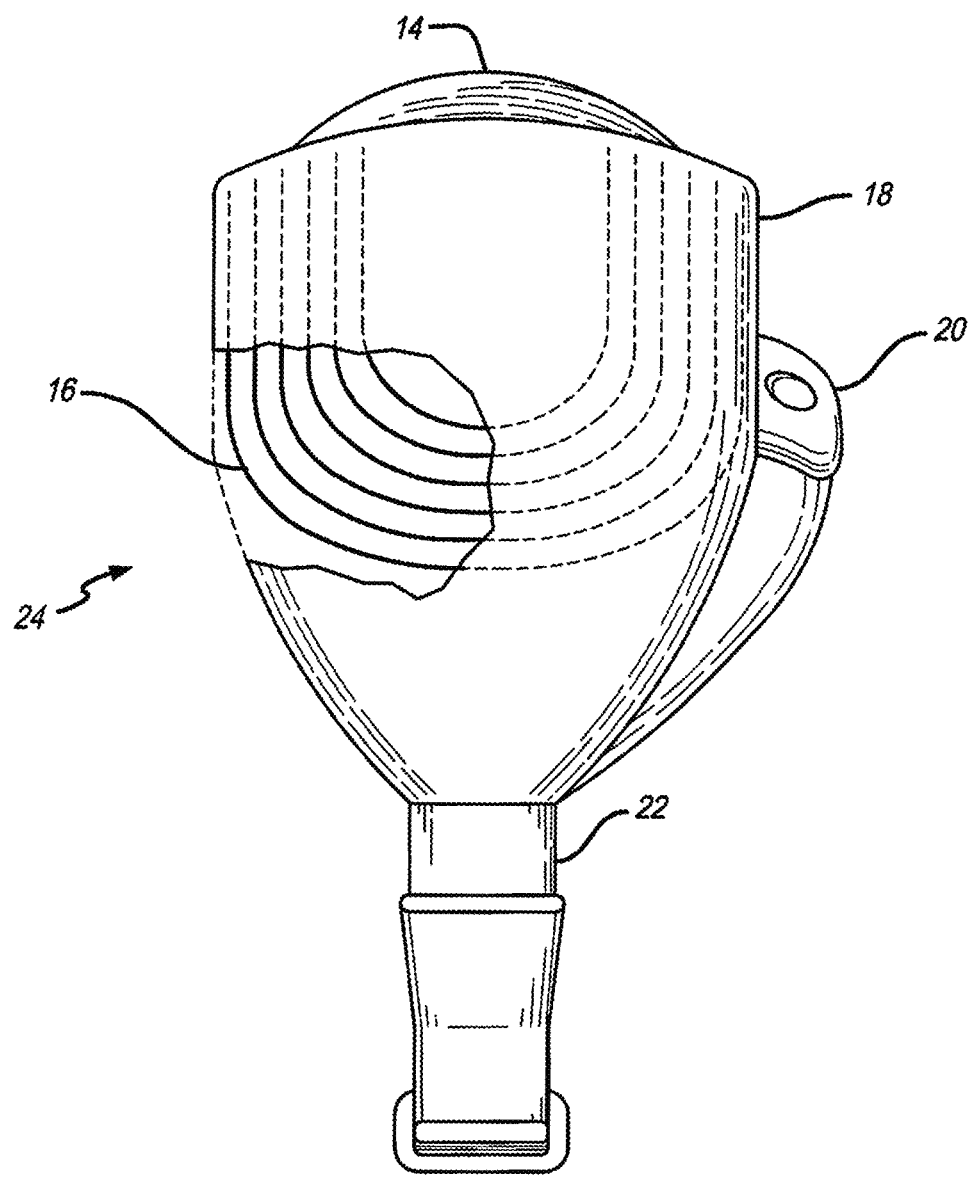
FIG. 8 is a side view of the implanted portion of the preferred visual prosthesis showing the strap fan tail in more detail.

FIGS. 7 and 8 present the general structure of a visual prosthesis used in implementing the invention.

FIG. 7 shows a perspective view of the implanted portion of the preferred visual prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22, which surrounds the sclera and holds the molded body 18, secondary inductive coil 16 and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 8 shows a side view of the implanted portion of the visual prosthesis, in particular, emphasizing the fan tail 24. When implanting the visual prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the visual prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 that aids the surgeon in passing the strap under the rectus muscles.

Figure 9:
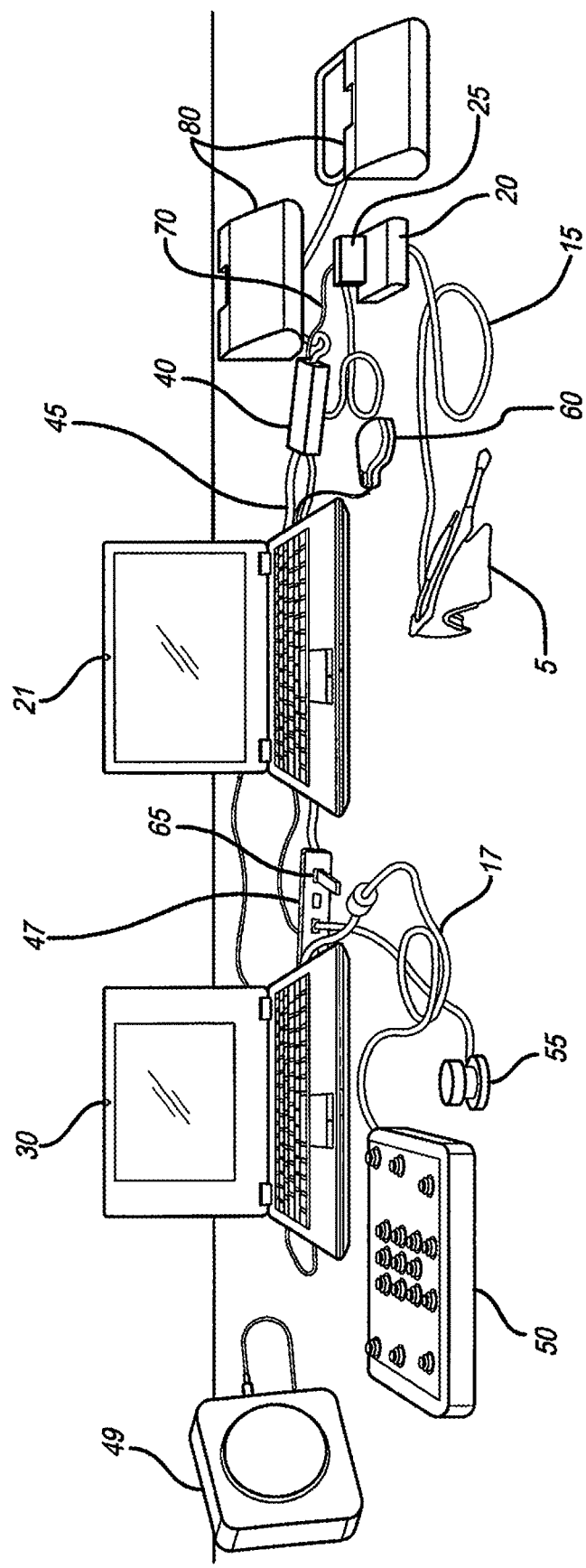
FIG. 9 shows the components of a visual prosthesis fitting system.

Referring to FIG. 9, a Fitting System (FS) may be used to configure and optimize the visual prosthesis 3 of the Retinal Stimulation System 1.

The Fitting System may comprise custom software with a Graphical User Interface (GUI) running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) 20 and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located, for example, on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record user responses. The PTS may include a collection of standard psychophysics experiments, developed using, for example, MATLAB (MathWorks) software and other tools, to allow the clinicians to develop customized psychophysics experiment scripts.

Any time stimulation is sent to the VPU 20, the stimulation parameters are checked to ensure that maximum charge per phase limits, charge balance, and power limitations are met before the test stimuli are sent to the VPU 20 to make certain that stimulation is safe.

Using the psychophysics module, important perceptual parameters, such as perceptual threshold, maximum comfort level, and spatial location of percepts, may be reliably measured.

Based on these perceptual parameters, the fitting software enables custom configuration of the transformation between video image and spatio-temporal electrode stimulation parameters in an effort to optimize the effectiveness of the visual prosthesis for each user.

The Fitting System laptop 10 is connected to the VPU 20 using an optically isolated serial connection adapter 40. Because it is optically isolated, the serial connection adapter 40 assures that no electric leakage current can flow from the Fitting System laptop 10.

As shown in FIG. 9, the following components may be used with the Fitting System according to the present disclosure. A Video Processing Unit (VPU) 20 for the user being tested, a Charged Battery 25 for the VPU 20, Glasses 5, a Fitting System (FS) laptop 10, a Psychophysical Test System (PTS) laptop 30, a PTS CD (not shown), a Communication Adapter (CA) 40, a USB Drive (Security) (not shown), a USB Drive (Transfer) (not shown), a USB Drive (Video Settings) (not shown), a User Input Device (RF Tablet) 50, a further User Input Device (Jog Dial) 55, Glasses Cable 15, CA-VPU Cable 70, CFS-CA Cable 45, CFS-PTS Cable 46, Four (4) Port USB Hub 47, Mouse 60, LED Test Array 80, Archival USB Drive 49, an Isolation Transformer (not shown), adapter cables (not shown), and an External Monitor (not shown).

The external components of the Fitting System according to the present disclosure may be configured as follows. The battery 25 is connected with the VPU 20. The PTS laptop 30 is connected to FS laptop 10 using the CFS-PTS Cable 46. The PTS laptop 30 and FS laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two User Input Devices 50 and 55 are connected to four (4) Port USB Hubs 47. The FS laptop 10 is connected to the Communication Adapter (CA) 40 using the CFS-CA Cable 45. The CA 40 is connected to the VPU 20 using the CA-VPU Cable 70. The Glasses 5 are connected to the VPU 20 using the Glasses Cable 15.

Stand-Alone Mode

Figure 10A:
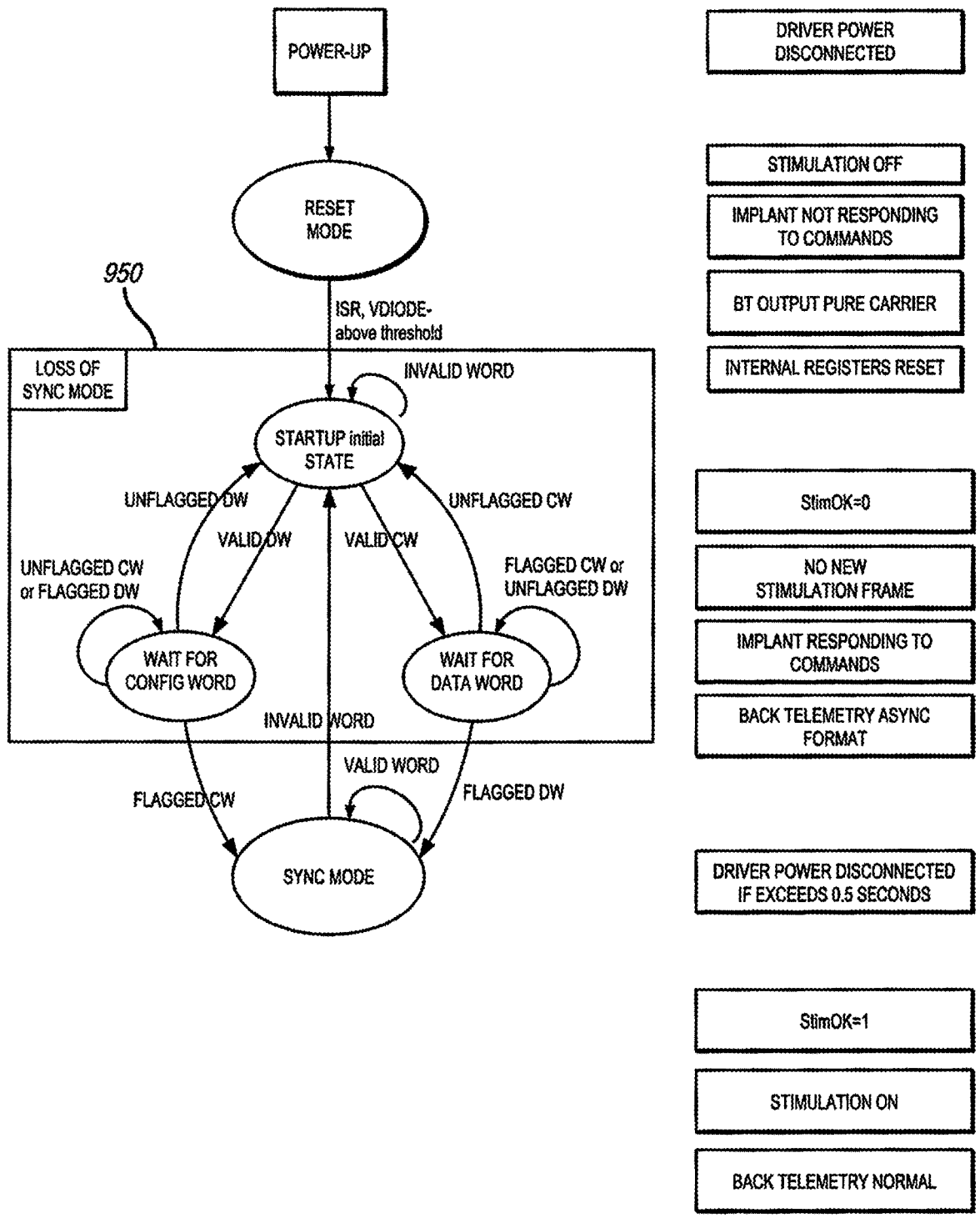
FIG. 10a shows a LOSS OF SYNC mode.

Referring to FIG. 10, in the stand-alone mode, the video camera 13 on the Glasses 5 captures a video image that is sent to the VPU 20. The VPU 20 processes the image from the camera 13 and transforms it into electrical stimulation patterns that are transmitted to the external coil 17. The external coil 17 sends the electrical stimulation patterns and power via radio-frequency (RF) telemetry to the implanted Retinal Stimulation System. The internal coil 16 of the Retinal Stimulation System receives the RF commands from the external coil 17 and transmits them to the electronics package 14 that in turn delivers stimulation to the retina via the electrode array 10. Additionally, the Retinal Stimulation System may communicate safety and operational status back to the VPU 20 by transmitting RF telemetry from the internal coil 16 to the external coil 17. The visual prosthesis apparatus may be configured to electrically activate the Retinal Stimulation System only when it is powered by the VPU 20 through the external coil 17. The stand-alone mode may be used for clinical testing and/or at-home use by the user.

Communication Mode

The communication mode may be used for diagnostic testing, psychophysical testing, user fitting and downloading of stimulation settings to the VPU 20 before transmitting data from the VPU 20 to the retinal stimulation system, as is done, for example, in the stand-alone mode described above. Referring to FIG. 9, in the communication mode, the VPU 20 is connected to the Fitting System (FS) laptop 21 using cables 70, 45 and the optically isolated serial connection adapter 40. In this mode, laptop 21 generated stimuli may be presented to the user and programming parameters may be adjusted and downloaded to the VPU 20. The Psychophysical Test System (PTS) laptop 30 connected to the Fitting System (FS) laptop 21 may also be utilized to perform more sophisticated testing and analysis as fully described in the related application, U.S. Pat. No. 8,271,091, which is incorporated herein by reference in its entirety.

In one embodiment, the functionality of the Retinal Stimulation System can also be tested pre-operatively and intra-operatively (i.e. before operation and during operation) by using an external coil 17 without the Glasses 5, placed in close proximity to the Retinal Stimulation System. The coil 17 may communicate the status of the Retinal Stimulation System to the VPU 20 that is connected to the Fitting System laptop 21 as shown in FIG. 9.

As discussed above, the VPU 20 processes the image from the camera 13 and transforms the image into electrical stimulation patterns for the Retinal Stimulation System. Filters, such as edge detection filters, may be applied to the electrical stimulation patterns, for example, by the VPU 20, to generate, for example, a stimulation pattern based on filtered video data that the VPU 20 turns into stimulation data for the Retinal Stimulation System. The images may then be reduced in resolution using a downscaling filter. In one exemplary embodiment, the resolution of the image may be reduced to match the number of electrodes in the electrode array 10 of the Retinal Stimulation System. That is, if the electrode array has, for example, sixty electrodes, the image may be reduced to a sixty channel resolution. After the reduction in resolution, the image is mapped to stimulation intensity using, for example, a look-up table that has been derived from testing of individual users. Then the VPU 20 transmits the stimulation parameters via forward telemetry to the Retinal Stimulation System in frames that may employ a cyclic redundancy check (CRC) error detection scheme.

In one exemplary embodiment, the VPU 20 may be configured to allow the user i) to turn the visual prosthesis apparatus on and off, ii) to manually adjust settings, and iii) to provide power and data to the Retinal Stimulation System. Referring again to FIGS. 1 through 4, the VPU 20 may comprise a case and buttons 6, including a power button for turning the VPU 20 on and off, a setting button and zoom buttons for controlling the camera 13, temple extensions 8 for connecting to the Glasses 5, a connector port for connecting to the laptop 21 through the connection adapter 40, one or more indicator lights (not shown) on the VPU 20 or Glasses 5 to give visual indication of the operating status of the system, the rechargeable battery (not shown) for powering the VPU 20, battery latch (not shown) for locking the battery in the case, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings to help the user identify the functionality of the button without having to look at it.

In one embodiment, the indicator lights may indicate that the VPU 20 is going through system start-up diagnostic testing when the one or more indicator lights are blinking fast (more than once per second) and are green in color. The indicator lights may indicate that the VPU 20 is operating normally when the one or more indicator lights are blinking once per second and are green in color. The indicator lights may indicate that the Retinal Stimulation System has a problem that was detected by the VPU 20 during the start-up diagnostic when the one or more indicator lights are blinking, for example, once in every five seconds, and are green in color. The indicator lights may indicate that there is a loss of communication between the Retinal Stimulation System and the external coil 17 due to the movement or removal of the Glasses 5 while the system is operational, or if the VPU 20 detects a problem with the Retinal Stimulation System and shuts off power to the Retinal Stimulation System when the one or more indicator lights are always on and are orange color. One skilled in the art would appreciate that other colors and blinking patterns can be used to give visual indication of the operating status of the system without departing from the spirit and scope of the invention.

In one embodiment, a single short beep from the speaker (not shown) may be used to indicate that one of the buttons 6 have been pressed. A single beep followed by two more beeps from the speaker (not shown) may be used to indicate that the VPU 20 is turned off. Two beeps from the speaker (not shown) may be used to indicate that the VPU 20 is starting up. Three beeps from the speaker (not shown) may be used to indicate that an error has occurred and the VPU 20 is about to shut down automatically. As would be clear to one skilled in the art, different periodic beeping may also be used to indicate a low battery voltage warning, that there is a problem with the video signal, and/or there is a loss of communication between the Retinal Stimulation System and the external coil 17. One skilled in the art would appreciate that other sounds can be used to give audio indication of the operating status of the system without departing from the spirit and scope of the invention. For example, the beeps may be replaced by an actual prerecorded voice indicating the operating status of the system.

In one exemplary embodiment, the VPU 20 is in constant communication with the Retinal Stimulation System through forward and backward telemetry. In this document, the forward telemetry refers to transmission from the VPU 20 to the Retinal Stimulation System and the backward telemetry refers to transmissions from the Retinal Stimulation System to the VPU 20. During the initial setup, the VPU 20 may transmit null frames (containing no stimulation information) until the VPU 20 synchronizes with the Retinal Stimulation System via the back telemetry. In one embodiment, an audio alarm may be used to indicate whenever the synchronization has been lost.

In order to supply power and data to the Retinal Stimulation System, the VPU 20 may drive the external coil 17, for example, with a 3 MHz signal. To protect the user, the Retinal Stimulation System may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the VPU's firmware. For the forward telemetry, this is due to the fact that a 16-bit cyclic redundancy check (CRC) is calculated for every 1024 bits sent to the ASIC within electronics package 14 of the Retinal Stimulation System. The ASIC of the Retinal Stimulation System verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Biphase Mark Encoded (BPM) data. If the VPU 20 detects invalid back telemetry data, the VPU 20 immediately changes mode to a 'safe' mode where the Retinal Stimulation System is reset and the VPU 20 only sends non-stimulating data frames. Back telemetry errors cannot cause the VPU 20 to do anything that would be unsafe.

The response to errors detected in data transmitted by VPU 20 may begin at the ASIC of the Retinal Stimulation System. The Retinal Stimulation System may be constantly checking the headers and CRCs of incoming data frames. If either the header or CRC check fails, the ASIC of the Retinal Stimulation System may enter a mode called LOSS OF SYNC 950, shown in FIG. 10a. In LOSS OF SYNC mode 950, the Retinal Stimulation System will no longer produce a stimulation output, even if commanded to do so by the VPU 20. This cessation of stimulation occurs after the end of the stimulation frame in which the LOSS OF SYNC mode 950 is entered, thus avoiding the possibility of unbalanced pulses not completing stimulation. If the Retinal Stimulation System remains in a LOSS OF SYNC mode 950 for 1 second or more (for example, caused by successive errors in data transmitted by the VPU 20), the ASIC of the Retinal Stimulation System disconnects the power lines to the stimulation pulse drivers. This eliminates the possibility of any leakage from the power supply in a prolonged LOSS OF SYNC mode 950. From the LOSS OF SYNC mode 950, the Retinal Stimulation System will not re-enter a stimulating mode until it has been properly initialized with valid data transmitted by the VPU 20.

In addition, the VPU 20 may also take action when notified of the LOSS OF SYNC mode 950. As soon as the Retinal Stimulation System enters the LOSS OF SYNC mode 950, the Retinal Stimulation System reports this fact to the VPU 20 through back telemetry. When the VPU 20 detects that the Retinal Stimulation System is in LOSS OF SYNC mode 950, the VPU 20 may start to send 'safe' data frames to the Retinal Stimulation System. 'Safe' data is data in which no stimulation output is programmed and the power to the stimulation drivers is also programmed to be off. The VPU 20 will not send data frames to the Retinal Stimulation System with stimulation commands until the VPU 20 first receives back telemetry from the Retinal Stimulation System indicating that the Retinal Stimulation System has exited the LOSS OF SYNC mode 950. After several unsuccessful retries by the VPU 20 to take the implant out of LOSS OF SYNC mode 950, the VPU 20 will enter a Low Power Mode (described below) in which the implant is only powered for a very short time. In this time, the VPU 20 checks the status of the implant. If the implant continues to report a LOSS OF SYNC mode 950, the VPU 20 turns power off to the Retinal Stimulation System and tries again later. Since there is no possibility of the implant electronics causing damage when it is not powered, this mode is considered very safe.

Due to an unwanted electromagnetic interference (EMI) or electrostatic discharge (ESD) event, the VPU 20 data, specifically the VPU firmware code in RAM, can potentially get corrupted and may cause the VPU 20 firmware to freeze. As a result, the VPU 20 firmware will stop resetting the hardware watchdog circuit, which may cause the system to reset. This will cause the watchdog timer to expire causing a system reset in, for example, less than 2.25 seconds. Upon recovering from the reset, the VPU 20 firmware logs the event and shuts itself down. The VPU 20 will not allow system usage after this occurs once. This prevents the VPU 20 code from freezing for extended periods of time and hence reduces the probability of the VPU sending invalid data frames to the implant.

Supplying power to the Retinal Stimulation System can be a significant portion of the VPU 20's total power consumption. When the Retinal Stimulation System is not within receiving range to receive either power or data from the VPU 20, the power used by the VPU 20 is wasted.

Power delivered to the Retinal Stimulation System may be dependent on the orientation of the coils 17 and 16. The power delivered to the Retinal Stimulation System may be controlled, for example, via the VPU 20, every 16.6 ms. The Retinal Stimulation System may report how much power it receives and the VPU 20 may adjust the power supply voltage of the RF driver to maintain a required power level on the Retinal Stimulation System. Two types of power loss may occur: 1) long term (>~1 second) and 2) short term (<~1 second). The long term power loss may be caused, for example, by a user removing the Glasses 5.

Figure 10B:
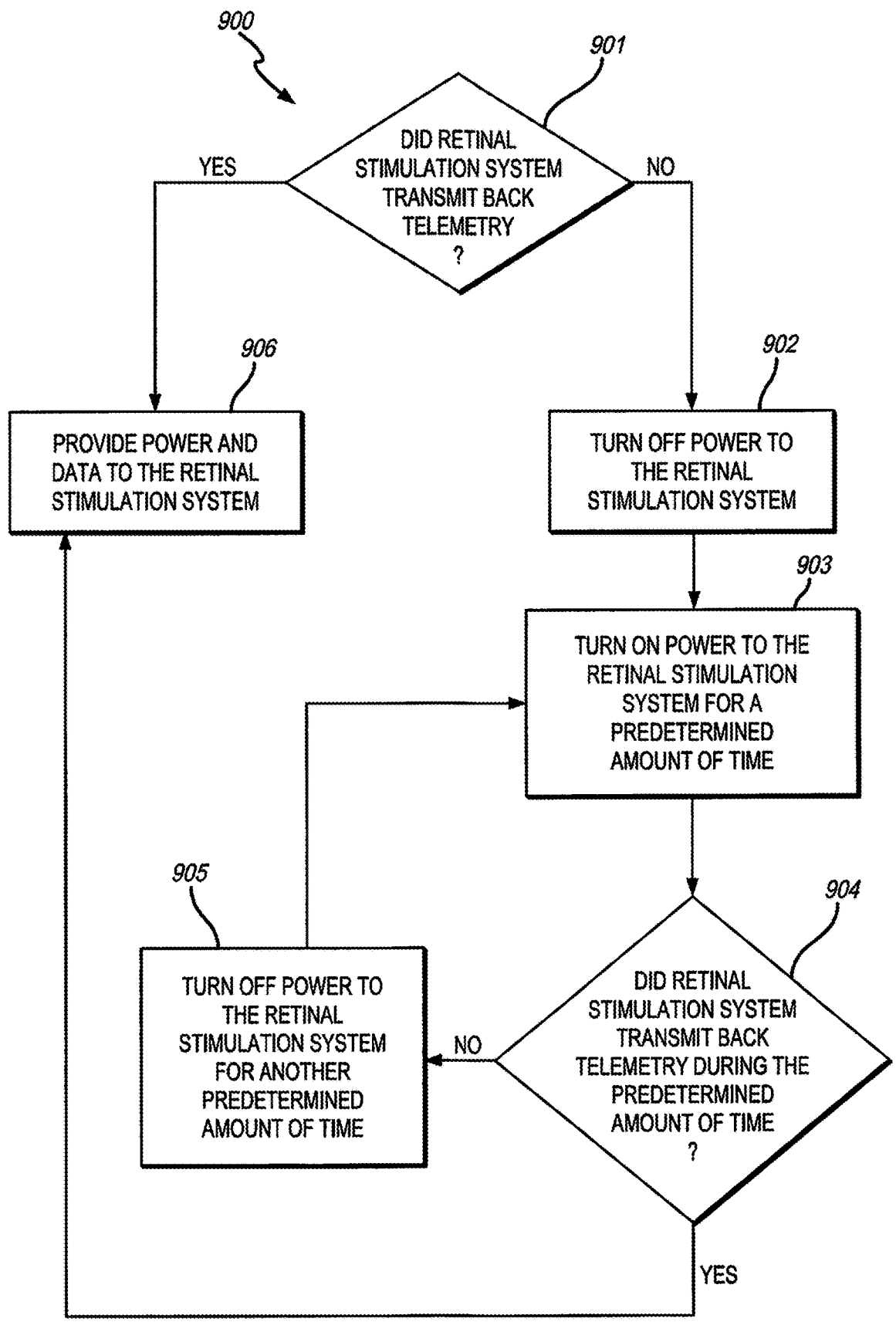
FIG. 10b shows an exemplary block diagram of the steps taken when VPU does not receive back telemetry from the Retinal Stimulation System.

In one exemplary embodiment, the Low Power Mode may be implemented to save power for the VPU 20. The Low Power Mode may be entered, for example, anytime the VPU 20 does not receive back telemetry from the Retinal Stimulation System. Upon entry into the Low Power Mode, the VPU 20 turns off power to the Retinal Stimulation System. After that, and periodically, the VPU 20 turns power back on to the Retinal Stimulation System for an amount of time just long enough for the presence of the Retinal Stimulation System to be recognized via its back telemetry. If the Retinal Stimulation System is not immediately recognized, the controller again shuts off power to the Retinal Stimulation System. In this way, the controller 'polls' for the passive Retinal Stimulation System and a significant reduction in power used is seen when the Retinal Stimulation System is too far away from its controller device. FIG. 10b depicts an exemplary block diagram 900 of the steps taken when the VPU 20 does not receive back telemetry from the Retinal Stimulation System. If the VPU 20 receives back telemetry from the Retinal Stimulation System (output "YES" of step 901), the Retinal Stimulation System may be provided with power and data (step 906). If the VPU 20 does not receive back telemetry from the Retinal Stimulation System (output "NO" of step 901), the power to the Retinal Stimulation System may be turned off. After some amount of time, power to the Retinal Stimulation System may be turned on again for enough time to determine if the Retinal Stimulation System is again transmitting back telemetry (step 903). If the Retinal Stimulation System is again transmitting back telemetry (step 904), the Retinal Stimulation System is provided with power and data (step 906). If the Retinal Stimulation System is not transmitting back telemetry (step 904), the power to the Retinal Stimulation System may again be turned off for a predetermined amount of time (step 905) and the process may be repeated until the Retinal Stimulation System is again transmitting back telemetry.

Figure 10C:
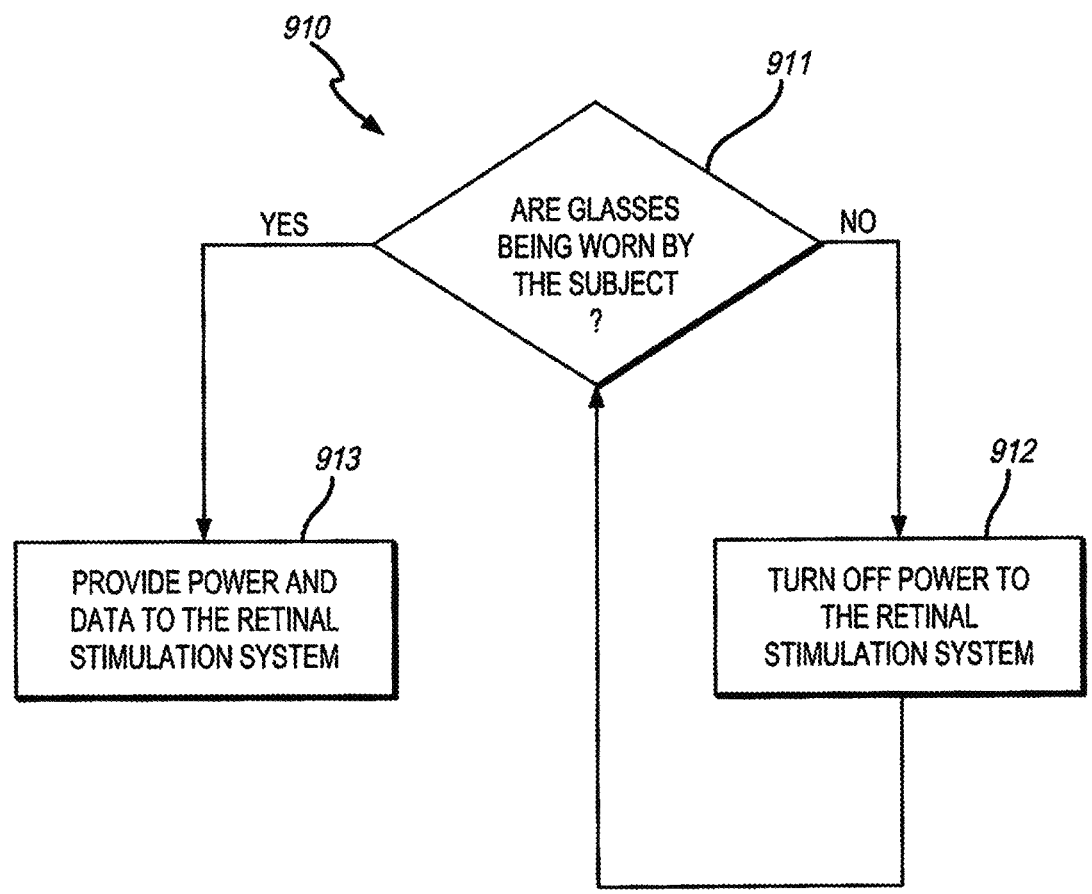
FIG. 10c shows an exemplary block diagram of the steps taken when the user is not wearing the Glasses.

In another exemplary embodiment, the Low Power Mode may be entered whenever the user is not wearing the Glasses 5. In one example, the Glasses 5 may contain a capacitive touch sensor (not shown) to provide the VPU 20 digital information regarding whether or not the Glasses 5 are being worn by the user. In this example, the Low Power Mode may be entered whenever the capacitive touch sensor detects that the user is not wearing the Glasses 5. That is, if the user removes the Glasses 5, the VPU 20 will shut off power to the external coil 17. As soon as the Glasses 5 are put back on, the VPU 20 will resume powering the external coil 17. FIG. 10c depicts an exemplary block diagram 910 of the steps taken when the capacitive touch sensor detects that the user is not wearing the Glasses 5. If the user is wearing the Glasses 5 (step 911), the Retinal Stimulation System is provided with power and data (step 913). If the user is not wearing the Glasses 5 (step 911), the power to the Retinal Stimulation System is turned off (step 912) and the process is repeated until the user is wearing the Glasses 5.

One exemplary embodiment of the VPU 20 is shown in FIGS. 11-1 to 11-4. The VPU 20 may comprise: a Power Supply Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I²C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer (not shown), an RF receiver 1065, and an RF transmitter 1070.

The Power Supply Distribution and Monitoring Circuit (PSDM) 1005 may regulate a variable battery voltage to several stable voltages that apply to components of the VPU 20. The Power Supply Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for the DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 13 into a down-scaled resolution digital image format. The Video Processor 1075 may comprise a video decoder (not shown) for converting the NTSC signal into a high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BCS) Control circuits. The video scaler may be composed of Acquisition control, Pre-scaler, BCS-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vice versa. The I²C Protocol Controller 1030 may also be connected to the Video Processor 1075 and the Real Time Clock 1060. The VPDI 1025 may contain a tri-state machine to shift video data from the Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR, BCLKR and BDR for the DSP 1020. The Input/Output Ports 1045 provide expanded JO functions to access the CPLD on-chip and off-chip devices. The Parallel Flash Memory (PFM) 1050 may be used to store executable code and the Serial Flash Memory (SFM) 1055 may provide a Serial Port Interface (SPI) for data storage. The VIMC may be used to sample and monitor RF transmitter 1070 current and voltage in order to monitor the integrity status of the Retinal Stimulation System.

Accordingly, what has been shown is an improved visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A visual prosthesis comprising:

A visible light camera suitable to be external to the body;

an infrared camera suitable to be external to the body;

a video processing unit receiving video data from the visible light camera and the infrared camera, the video processing unit combining video data from the infrared camera and the visible light camera, producing an input image having an input field of view, and producing an output image having an output field of view smaller than the input field of view, in the form of stimulation codes indicating electrode patterns to be presented;

the video processing unit including a pattern detection component detecting predetermined patterns in the input image;

a wireless transmitter receiving codes from the video processing unit and transmitting the codes;

an implantable wireless receiver suitable to be implanted within a body, receiving the codes from the wireless transmitter;

an implantable signal generator receiving the codes from the wireless receiver and generating stimulation signals; and an implantable electrode array receiving the stimulation signals and suitable to stimulate visual neural tissue;

wherein the pattern detection component provides an indication of a detected predetermined pattern in the stimulation signal.

2. The visual prosthesis according to claim 1, wherein the pattern detection component detects faces.

3. The visual prosthesis according to claim 1, wherein the pattern detection component detects heat hazards.

4. The visual prosthesis according to claim 1, further comprising a zoom component adapted to zoom out when the pattern is detected in an input field of view of the video data, but not an output field of view defined by the stimulation signals.

5. The visual prosthesis according to claim 4, wherein the zoom component and pattern detection component are manually operable.

6. The visual prosthesis according to claim 4, wherein the pattern detection component is continuous and cues a user to manually operate the zoom component.

7. The visual prosthesis according to claim 4, wherein the pattern detection component is continuous and automatically activates the zoom component in response to a detected pattern.

8. The visual prosthesis according to claim 7, wherein the visual prosthesis cues a user in response to the zoom component being automatically activated.

9. The visual prosthesis according to claim 1, further comprising a pattern recognition component recognizing features of the detected pattern.

10. The visual prosthesis according to claim 9, wherein the pattern recognition component includes a look up table of patterns and identifying information.

11. The visual prosthesis according to claim 10, wherein the look up table associates faces with names.

12. The visual prosthesis according to claim 11, further comprising an enunciator to announce a name associated with a detected face.

* * * * *